(12) United States Patent
Mernoe

(10) Patent No.: US 7,713,238 B2
(45) Date of Patent: May 11, 2010

(54) MEDICINE DISPENSING DEVICE

(75) Inventor: Morten Mernoe, Charlottenlund (DK)

(73) Assignee: M2 Group Holdings, Inc., Sunnyvale, CA (US)

( * ) Notice: Subject to any disclaimer, the term of this patent is extended or adjusted under 35 U.S.C. 154(b) by 710 days.

(21) Appl. No.: 10/591,190

(22) PCT Filed: Apr. 6, 2006

(86) PCT No.: PCT/DK2006/000195

§ 371 (c)(1),
(2), (4) Date: Aug. 31, 2006

(87) PCT Pub. No.: WO2006/105794

PCT Pub. Date: Oct. 12, 2006

(65) Prior Publication Data

US 2007/0185449 A1 Aug. 9, 2007

(30) Foreign Application Priority Data

| Apr. 6, 2005 | (DK) | ................................ | 2005 00483 |
| Apr. 14, 2005 | (DK) | ................................ | 2005 00542 |
| Jun. 3, 2005 | (DK) | ................................ | 2005 00817 |

(51) Int. Cl.
*A61M 37/00* (2006.01)

(52) U.S. Cl. .................................................. 604/131

(58) Field of Classification Search ................ 604/131, 604/151–155, 207–211, 174; 128/DIG. 1, 128/DIG. 12
See application file for complete search history.

(56) References Cited

U.S. PATENT DOCUMENTS

| 2,605,765 A | 8/1952 | Kollsman |
| 3,886,938 A | 6/1975 | Szabo et al. |
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |

(Continued)

FOREIGN PATENT DOCUMENTS

CA 2543545 5/2005

(Continued)

OTHER PUBLICATIONS

Patent Abstracts of Japan, vol. 1999, No. 04, and JP 11 010036, Apr. 30, 1999 and Jan. 19, 1999, Toray Ind. Inc.

(Continued)

*Primary Examiner*—Nicholas D Lucchesi
*Assistant Examiner*—Theodore J Stigell
(74) *Attorney, Agent, or Firm*—Fish & Richardson P.C.

(57) ABSTRACT

Some embodiments of a wearable, disposable medicine dispensing device may include a piston rod that is advanced to dispense medicine from the device. A rotational motor may be coupled to a drive mechanism so as to carry out a certain number of revolutions and thereby displace the piston rod by a desired distance. Such a device can be used in a method of dispensing liquid medicine.

35 Claims, 16 Drawing Sheets

U.S. PATENT DOCUMENTS

| | | |
|---|---|---|
| 4,529,401 A | 7/1985 | Leslie et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |

| | | |
|---|---|---|
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,144,384 B2 * | 12/2006 | Gorman et al. ............ 604/131 |
| 7,232,423 B2 | 6/2007 | Mernoe |
| 7,534,226 B2 * | 5/2009 | Mernoe et al. ............ 604/155 |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |

FOREIGN PATENT DOCUMENTS

| | | |
|---|---|---|
| DE | 196 27 619 A | 1/1998 |
| DE | 102 36 669 A | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/039763 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |

OTHER PUBLICATIONS

Medtronic News Release, "Medtronic Receives FDA Approval for World's First Insulin Pump with Real-time Continuous Glucose Monitoring," Apr. 13, 2006, 3 pages.
Debiotech News Release, "Debiotech reveals its new miniaturized Disposable Insulin Nanopump™ for Diabetes therapy," available at http://www.debiotech.com/news/nw_159.html, Apr. 24, 2006, 3 pages.
Accu-Chek Spirit, "Pump Therapy Made for You," Roche, 2006, 6 pages.
Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.
The Medtronic Diabetes Connection, 2006, 6 pages.
OmniPod Insulin Management System-Investor Relations- Press Release, Feb. 1, 2005, http://investors.insulet.com/phoenix.zhtml?c=209336&p=irol-newsArticle&ID=988708&highlight=1 page.
OmniPod Quick Start Guide, 2007, 2 pages.

* cited by examiner

MEDICINE DISPENSING DEVICE

This application is a national stage application under 35 U.S.C. §371 that claims the benefit of PCT/DK2006/000195 filed on Apr. 6, 2006 and entitled "An Actuator," which claims priority to the following Denmark patent applications: serial no. PA 2005 00483 filed on Apr. 6, 2005, serial no. PA 2005 005423 filed on Apr. 14, 2005, and serial no. PA 2005 00817 filed on Jun. 3, 2005. The entire contents of these prior applications are incorporated herein by reference.

The present invention relates to a method of dispensing liquid medicine comprising the steps of providing a wearable, disposable dispensing device comprising a syringe having a cylinder and a plunger displaceable in said syringe cylinder for pressing medicine out of said syringe cylinder and a drive mechanism connected to said plunger for displacing said plunger in said cylinder, and an electrical motor connected to a battery and to said drive mechanism for providing a rotary force to said driving mechanism for displacing said plunger, displacing said plunger a certain distance in connection with a cycle of said driving mechanism.

Methods of this type are known, wherein the electrical motor is controlled by a control means so as to carry out a certain number of revolutions for each cycle corresponding to the desired distance of displacement of the plunger.

In connection with such methods it is important that no more than the predetermined amount of medicine be dispensed per cycle as otherwise life threatening dosages may be dispensed.

When utilizing an electrical motor, a short circuit can entail that the motor does not stop after the predetermined number of revolutions or that the motor starts by itself.

Security means have been suggested to ensure that the predetermined dosage is not exceeded, for instance monitoring the amount of liquid dispensed per cycle or monitoring the displacement distance of the plunger or the amount of revolutions of the motor per cycle with interruption means being activated if the monitored elements exceed a certain value.

There exists a need for a simple and fail-safe method to avoid over-dosage of medicine. One main object of the invention is to meet this need.

According to the invention this object is achieved by the cycle comprising rotating said electrical motor in a first direction of rotation and subsequently rotating said electrical motor in the opposite direction of rotation.

Hereby, any short-circuit of the motor will not entail continued rotation of the motor in one direction with ensuing continued dispensing of medicine.

The invention furthermore relates to a wearable, disposable medicine dispensing device comprising:
  a syringe having cylinder and a plunger displaceable in the syringe cylinder for pressing medicine out of said syringe cylinder,
  a drive mechanism connected to said plunger for displacing said plunger in said cylinder, and
  an electrical motor connected to a battery and to said drive mechanism for providing a rotary force to said driving mechanism for displacing said plunger, and
  control means adapted for repeatedly reversing the direction of rotation of said electrical motor.

In a further aspect, the present invention relates to an actuator comprising:
  a rotational motor.
  one or more elongate, flexible elements such as a string, a filament, a strip, a ribbon and combinations thereof, said one or more elements being attached to said motor for rotation thereby and to a displaceable body, such that rotation of said motor twists said one or more elements and shortens the overall length thereof so that said displaceable body is displaced by the shortened element or elements.

Such an actuator according to the invention may be used in connection with medicine dispensing devices, but also in any application where a rotational force or movement is to be utilized to displace a body.

DESCRIPTION OF DRAWINGS

In the following the invention will be described more in detail in connection with two embodiments shown, solely by way of example, in the accompanying drawings, where.

DETAILED DESCRIPTION OF ILLUSTRATIVE EMBODIMENTS

Figure 1:
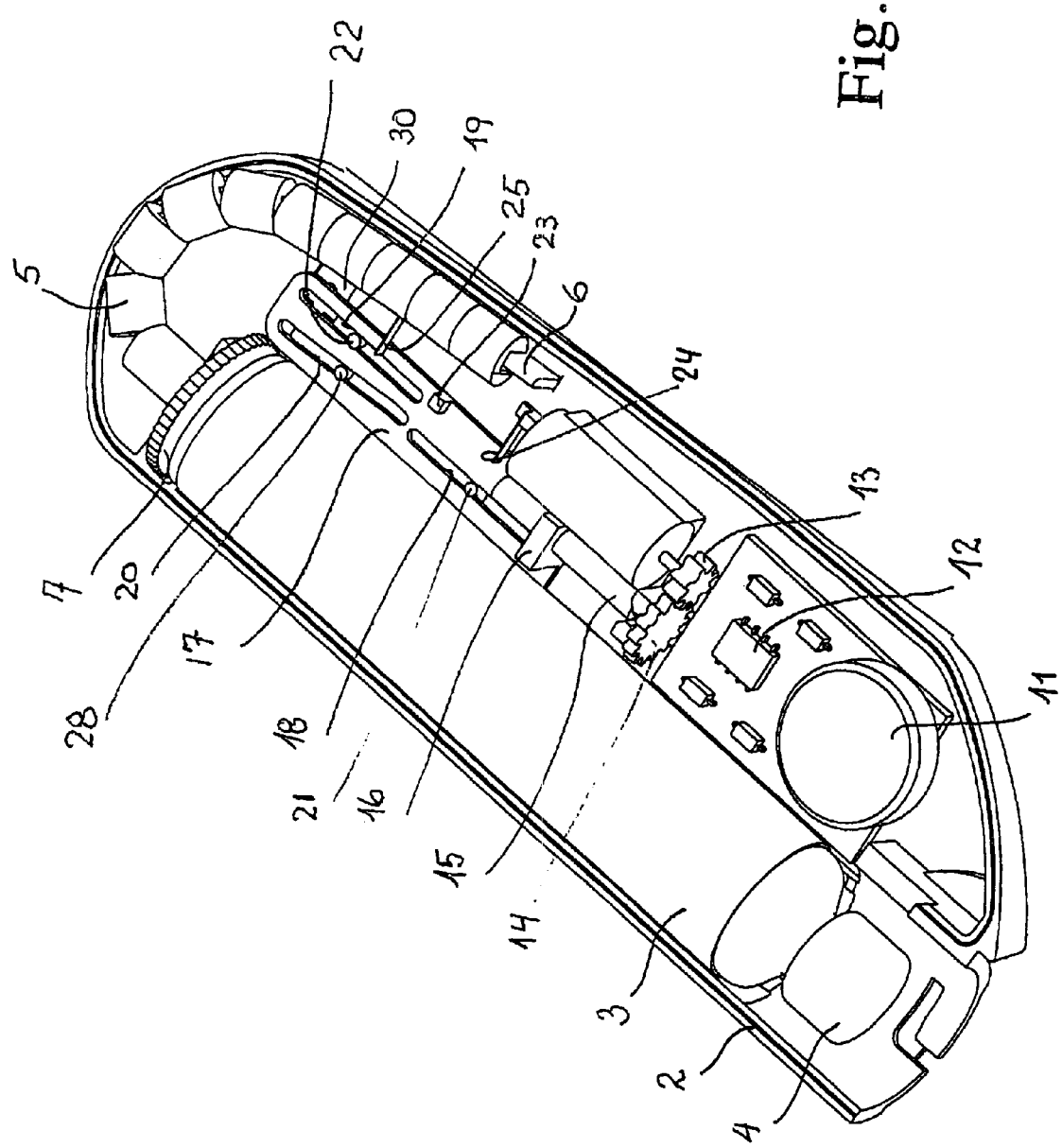
FIG. 1 shows a first embodiment of a device according to the invention seen in perspective and with the top part of the housing removed.
Figure 2:
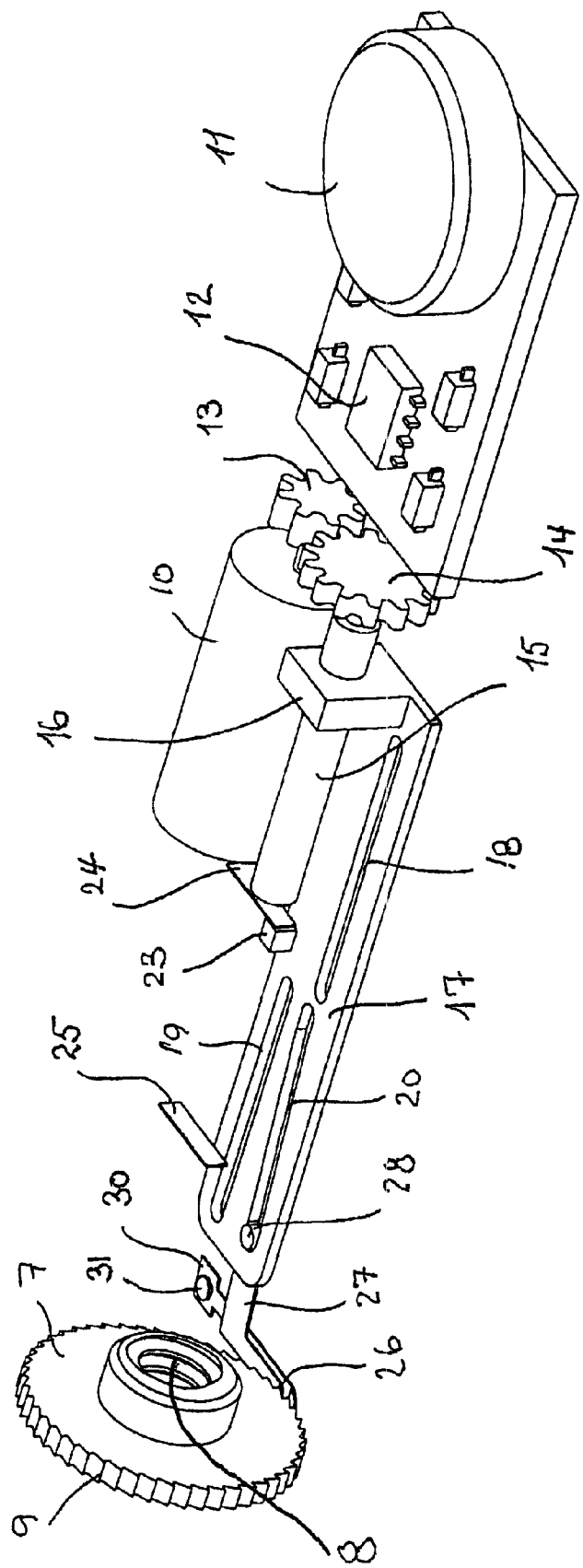
FIG. 2 shows a perspective view of the drive mechanism of the device according to the invention in FIG. 1.
Figure 3:
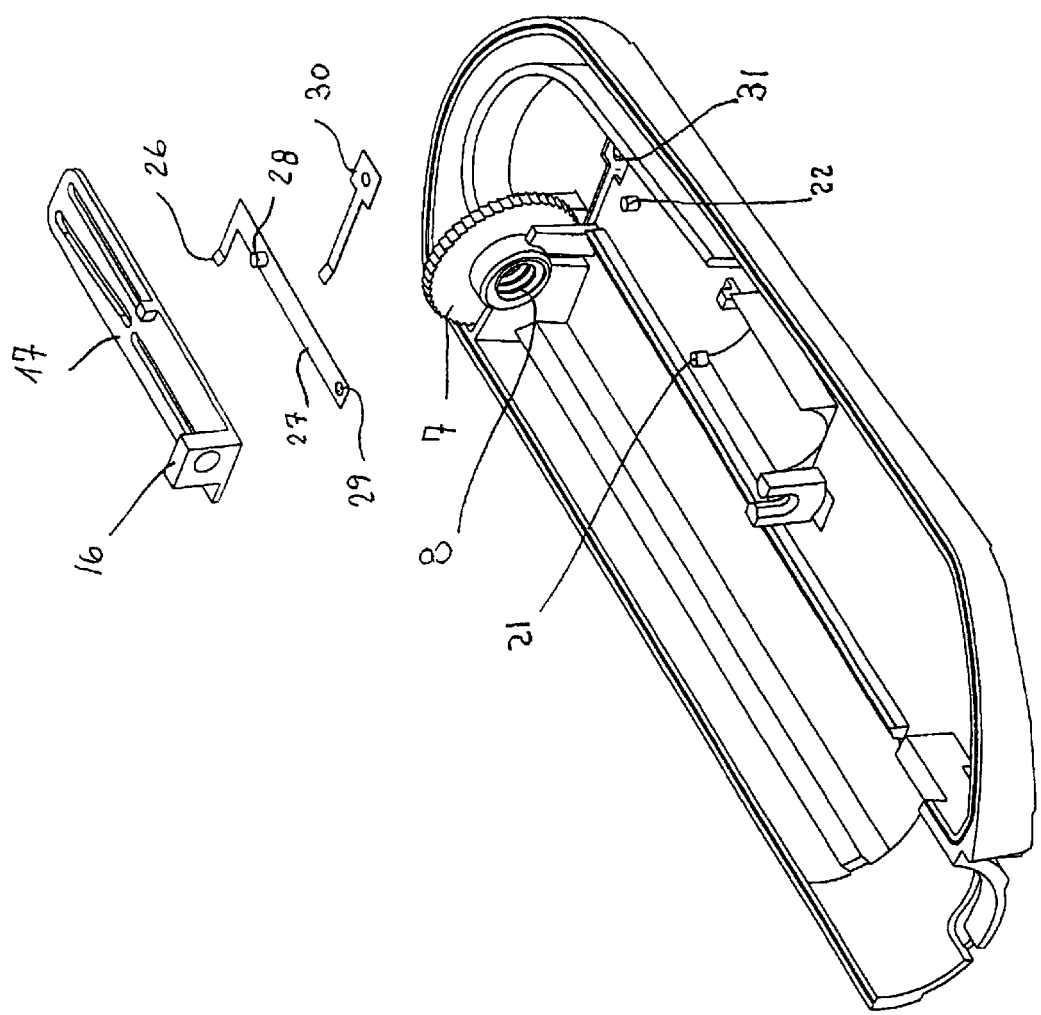
FIG. 3 is an exploded View of some of the drive mechanism elements of the device in FIG. 1, and FIGS. 4 and 5 are views corresponding to FIG. 2 with the drive mechanism in other positions.
Figure 4:
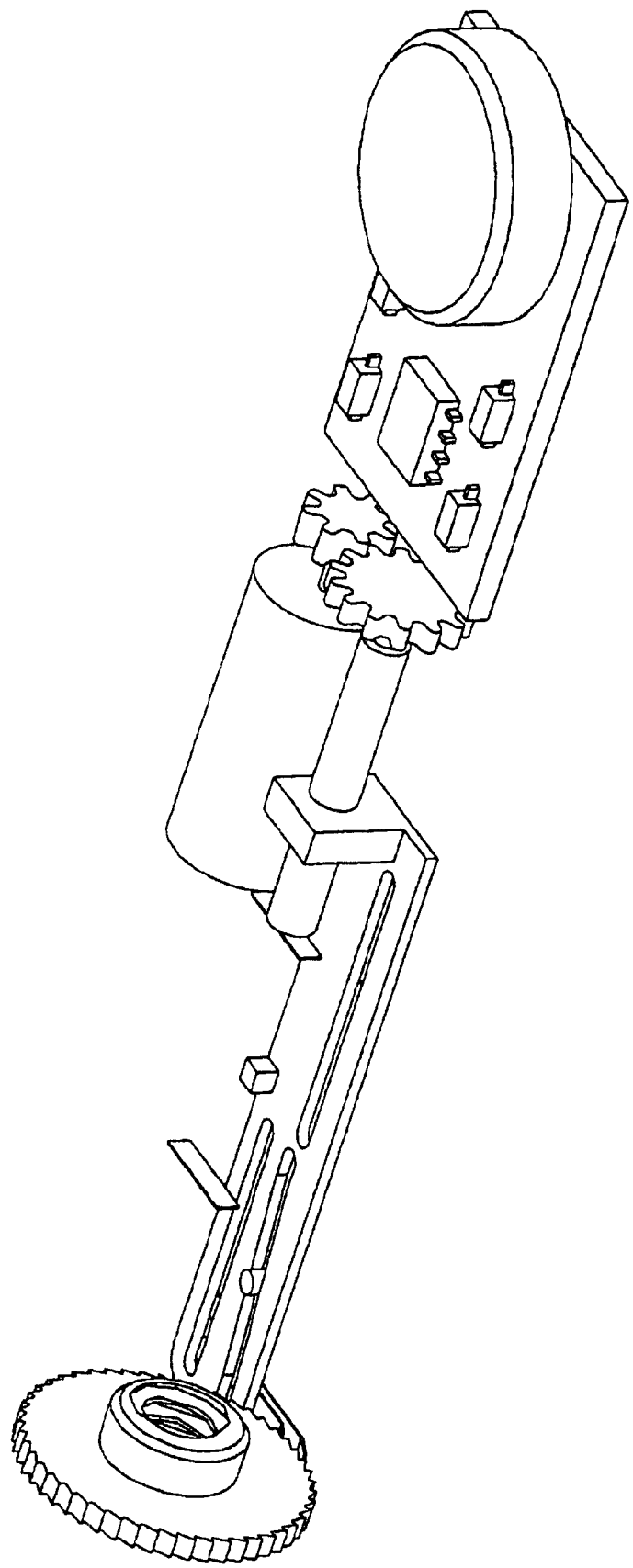
Figure 5:
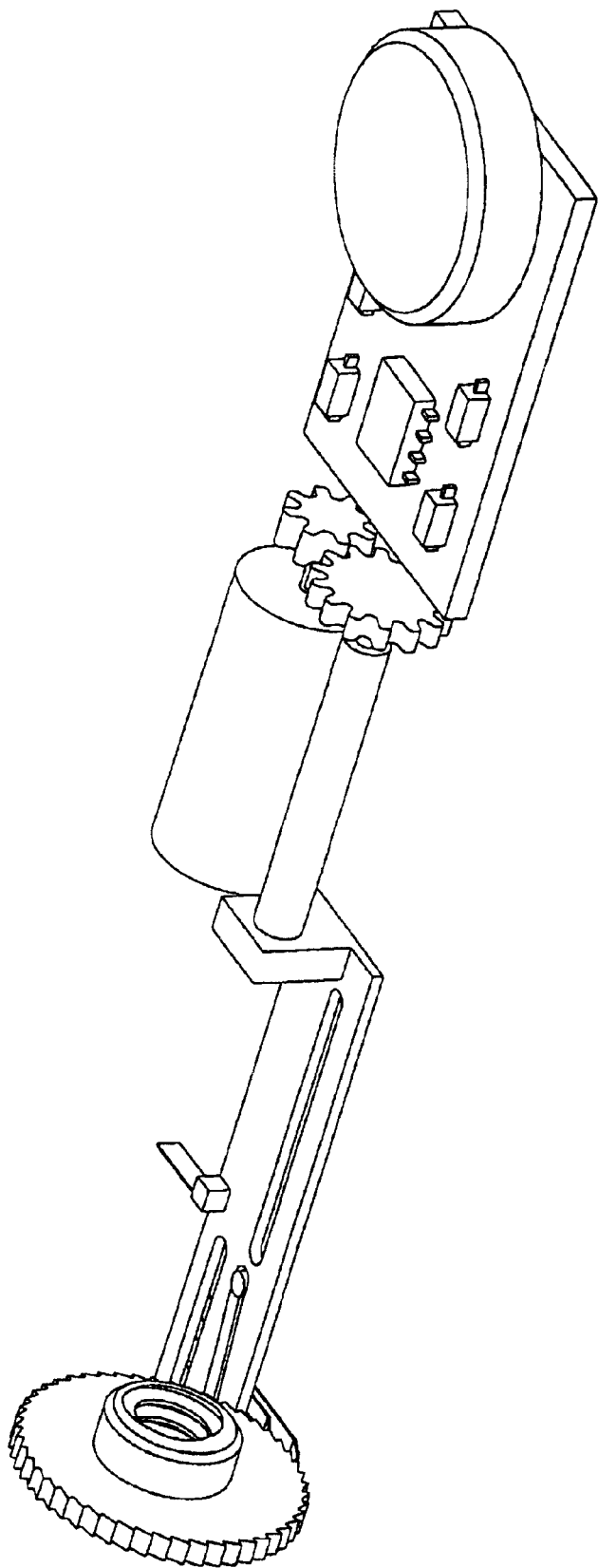
Figure 6:
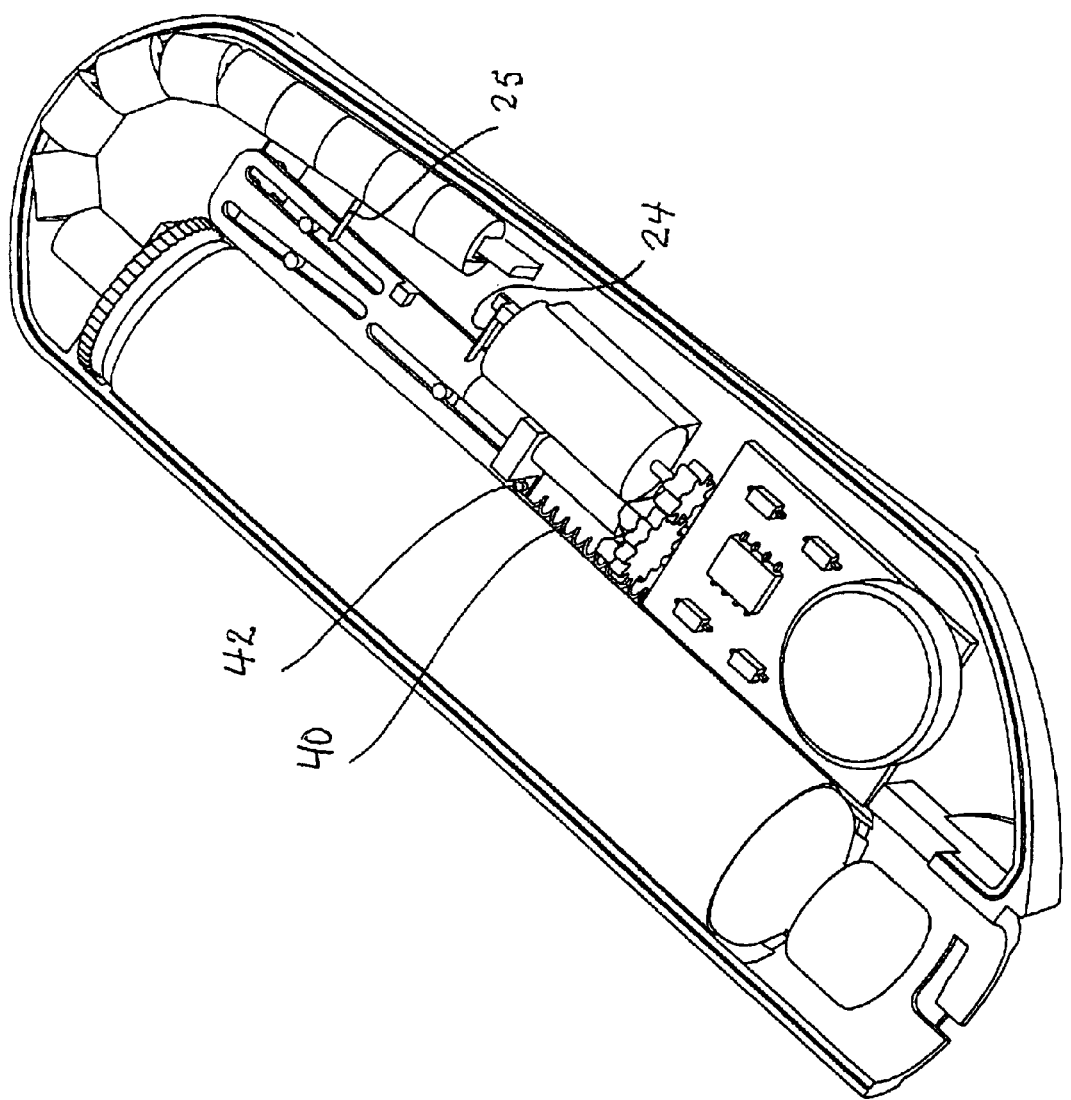
FIGS. 6-9 are views of a second embodiment of the device according to the invention corresponding to FIGS. 1, 2, 4 and 5, respectively.
Figure 7:
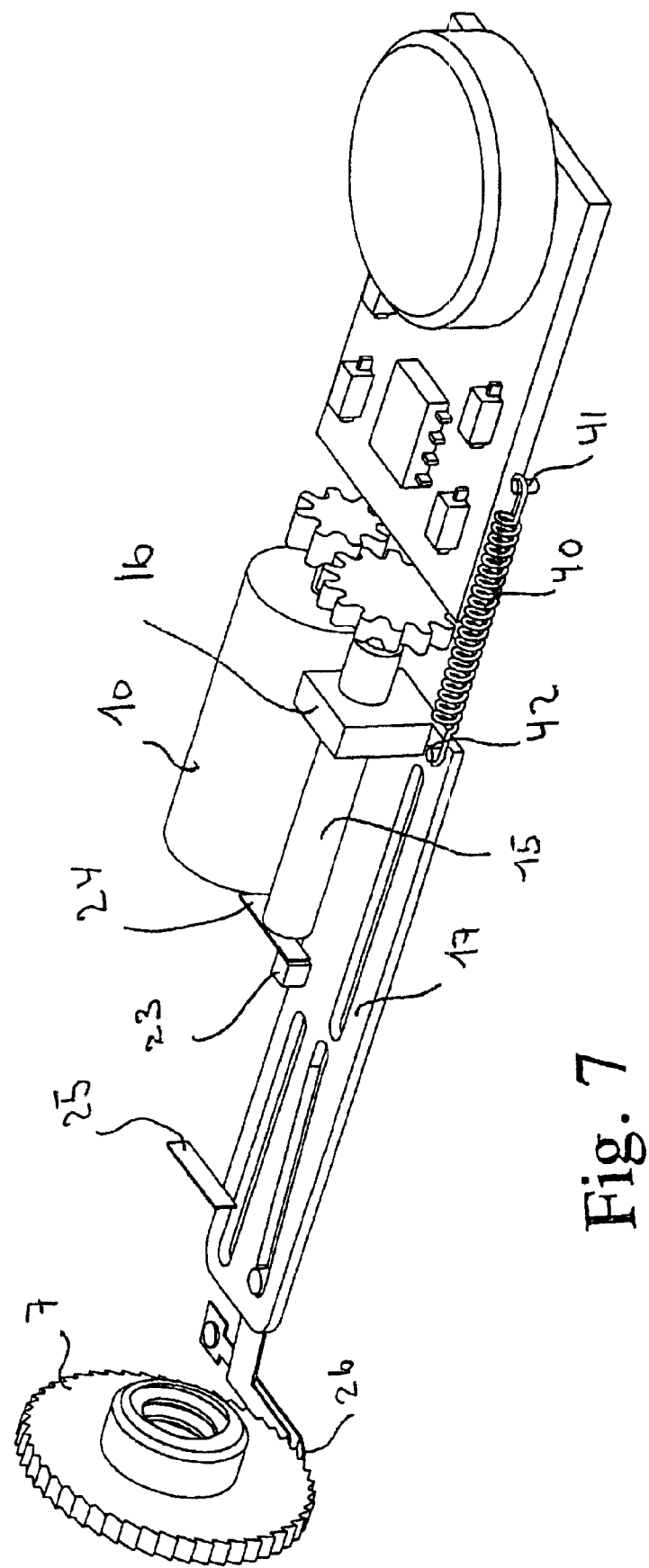
Figure 8:
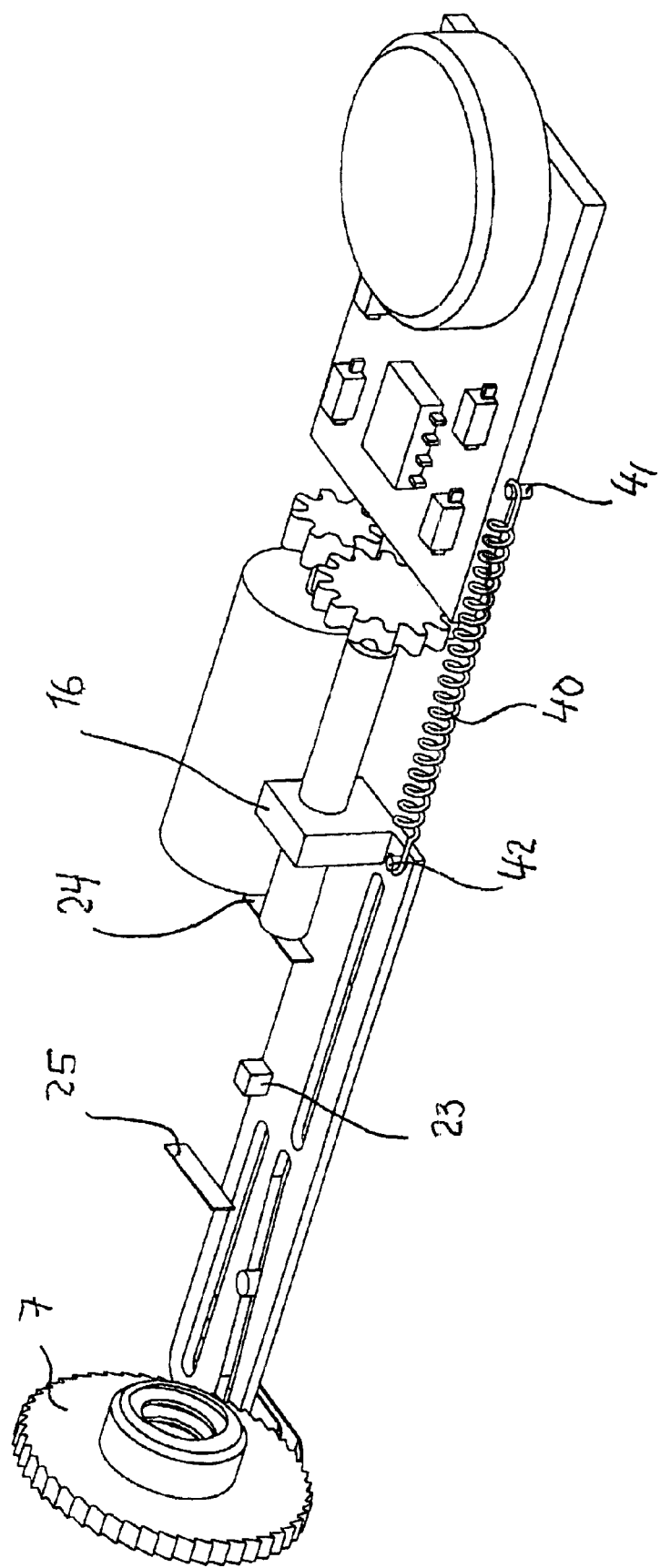
Figure 9:
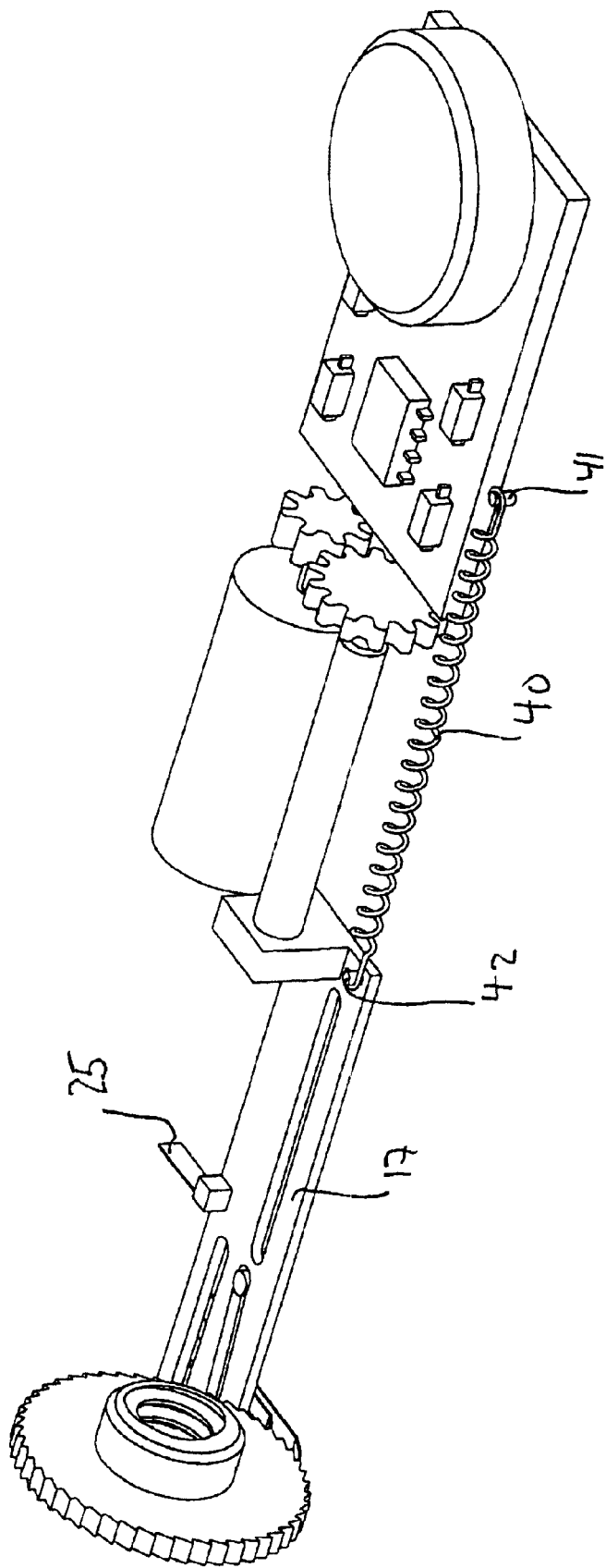
Figure 10:
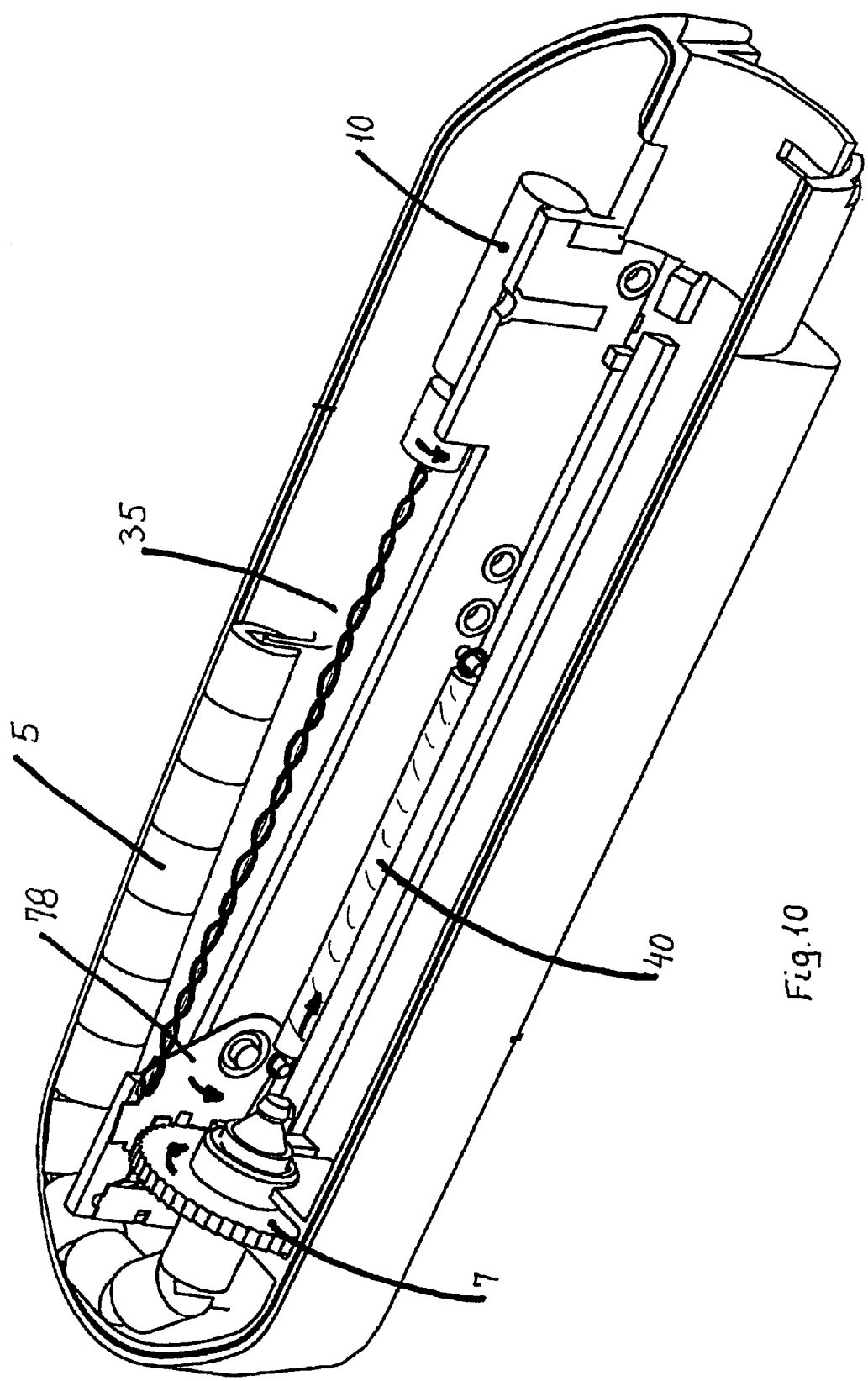
FIGS. 10-14 show a perspective view of a third embodiment of the device according to the invention in different sequential states during a first half cycle during rotation of the electrical motor in a first direction of rotation, FIGS. 15a, b and c are views of some of the drive mechanism elements of the device in FIGS. 10-14 in different states during the cycle.
Figure 11:
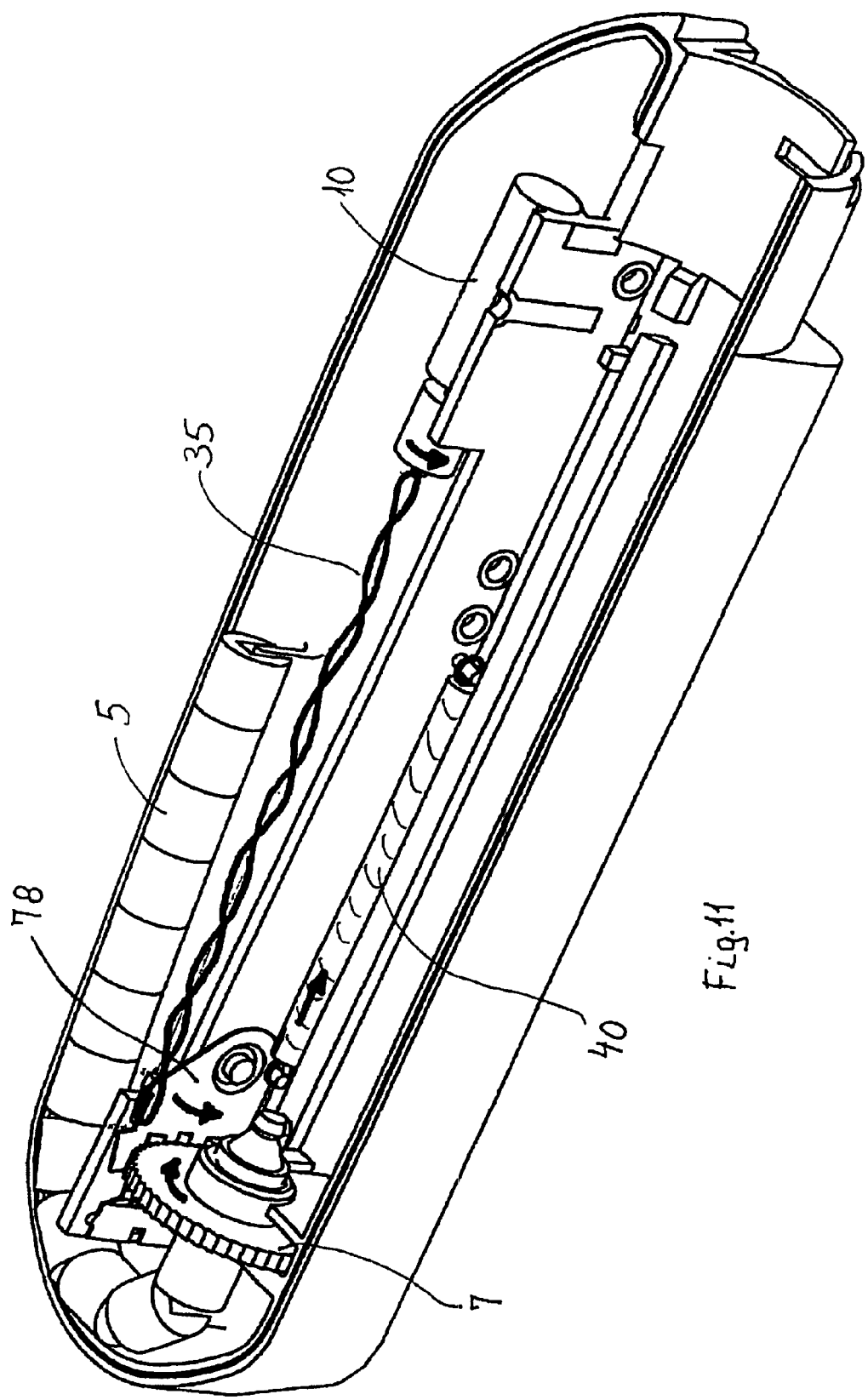
Figure 12:
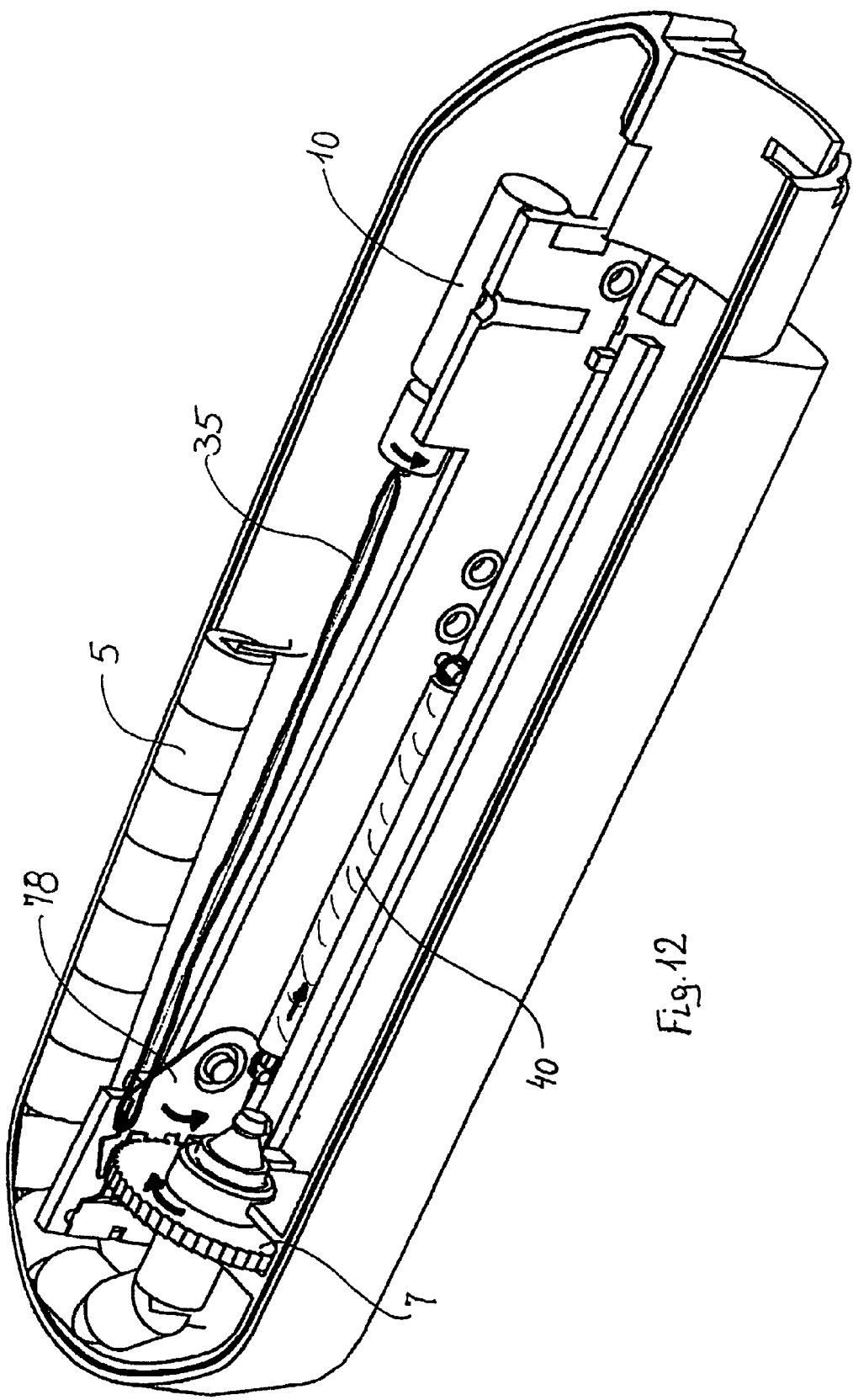
Figure 13:
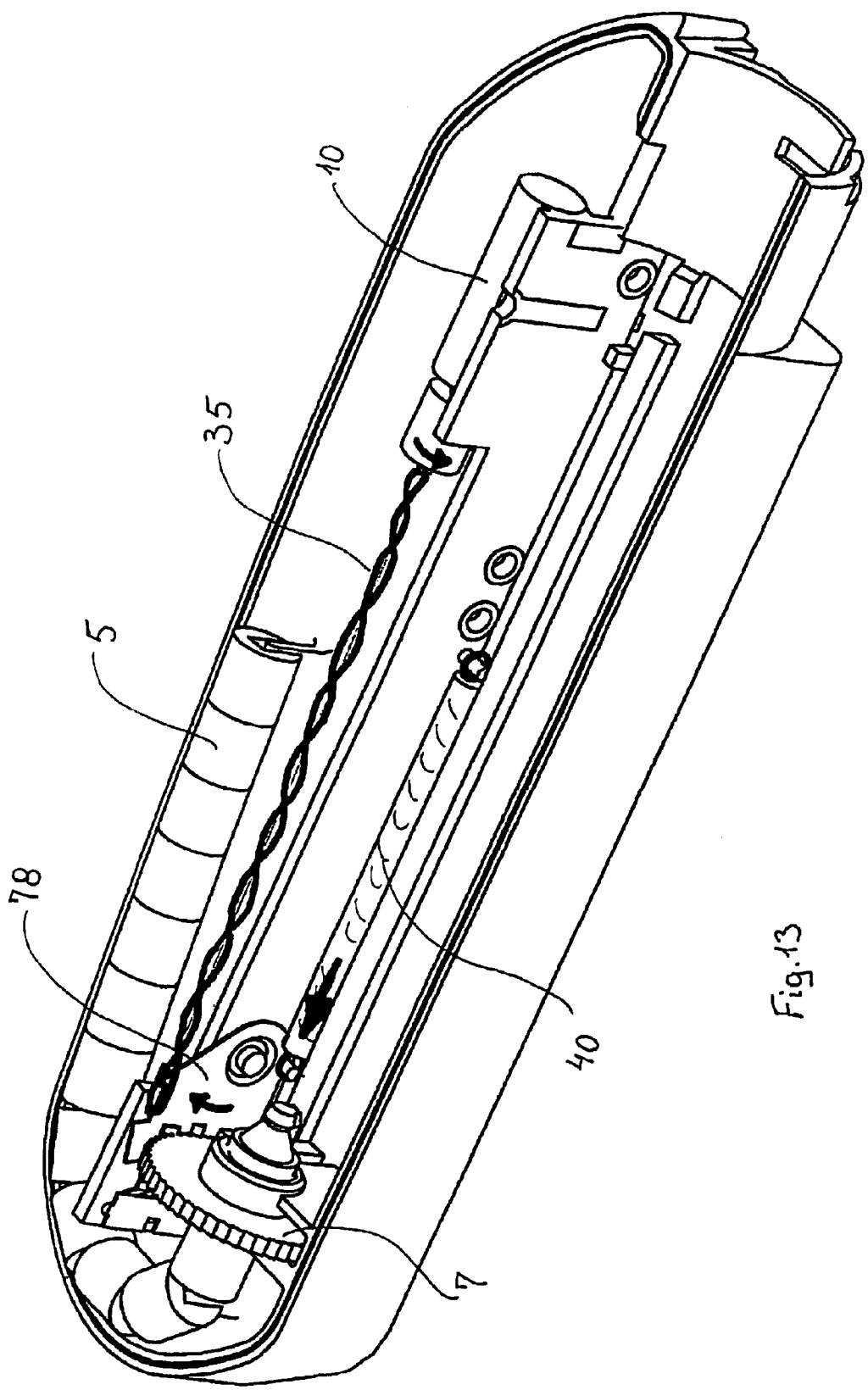
Figure 14:
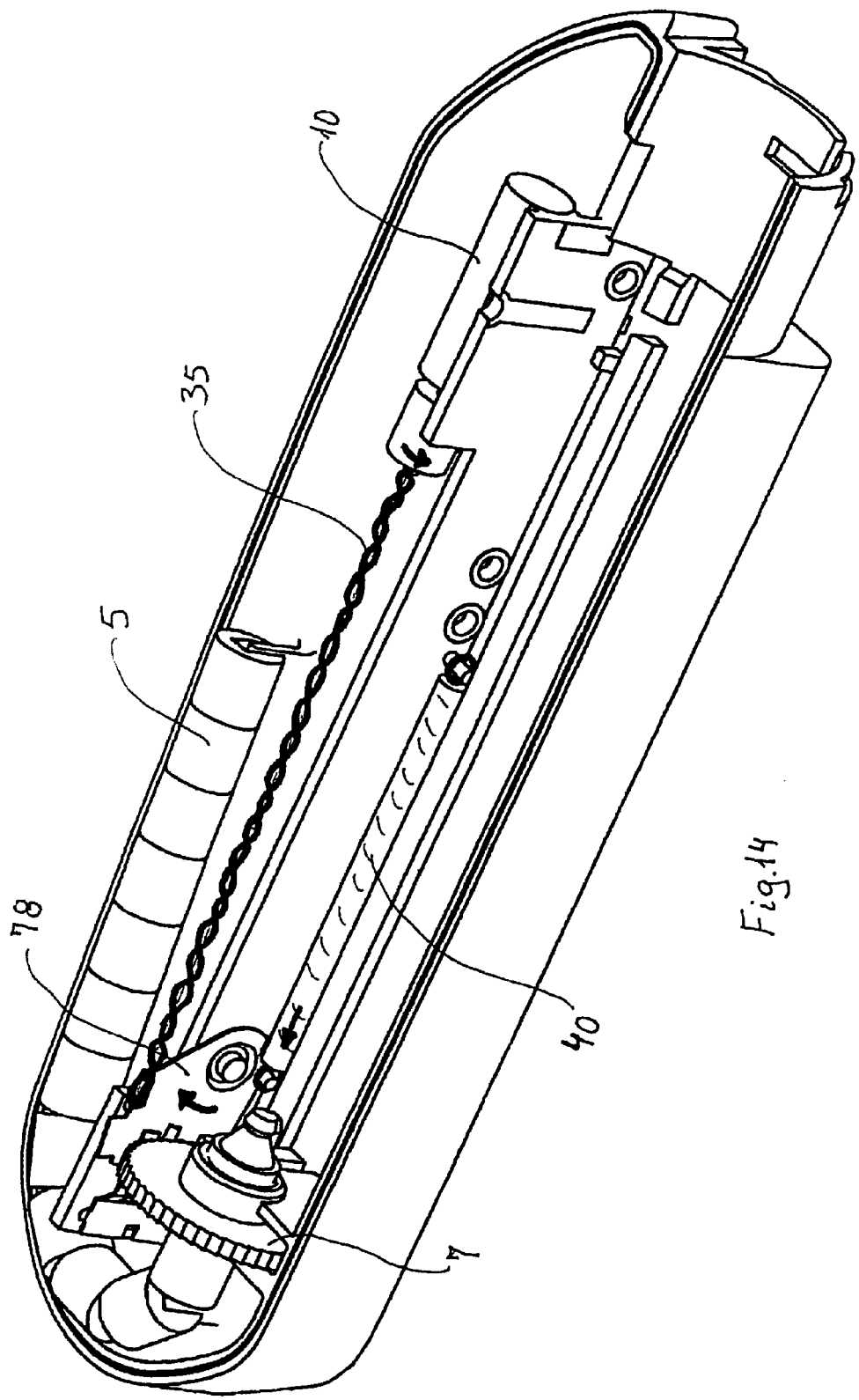
Figure 15:
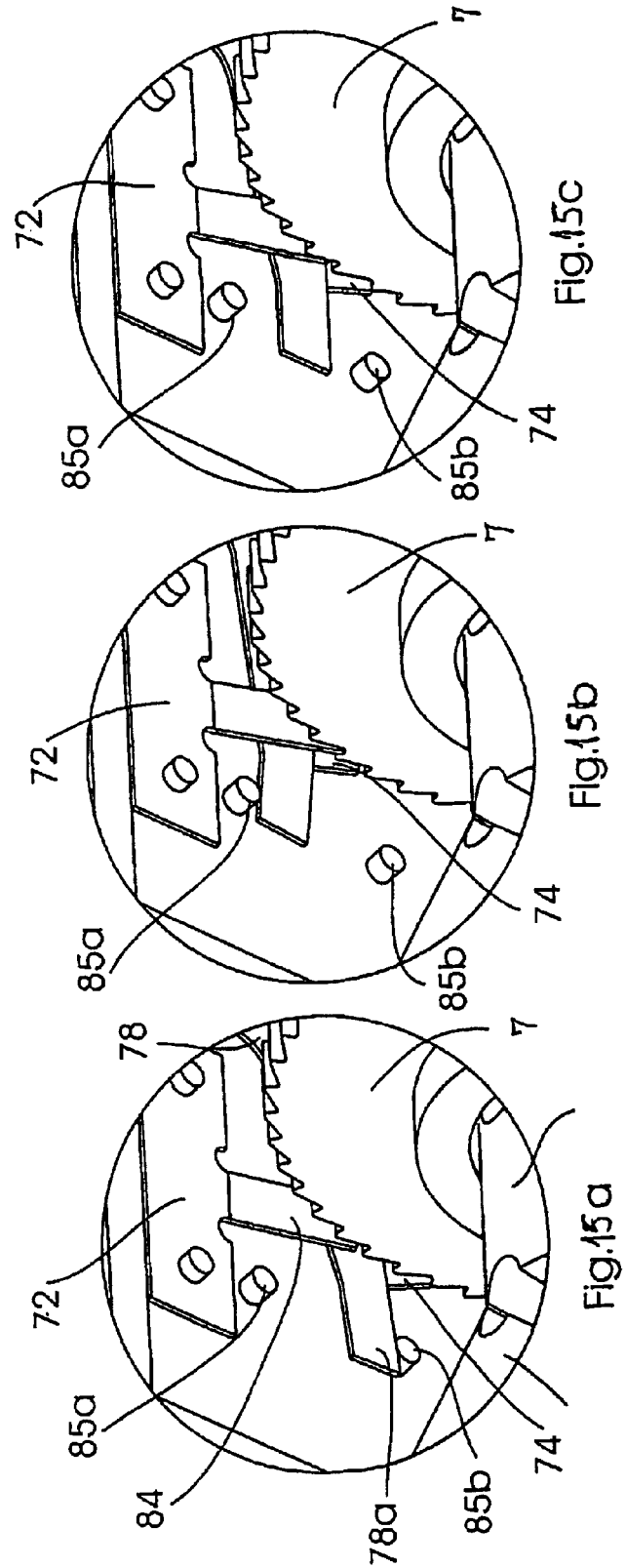

Referring now to FIGS. 1-5, a wearable disposable dispensing device for medicine referred to generally by the numeral 1 and of the type described in WO 2004/041330 and WO 2004/056412, the disclosure of which is hereby incorporated herein by reference, comprises a housing 2, where only the bottom half is shown for the sake of clarity, a cylindrical medicine container or carpule 3 having at one end a silicone body for receiving a catheter for dispensing medicine from the interior of the carpule to a human body and being open at the opposite end to receive a flexible piston rod 5 for displacing an internal not shown plunger or piston in the carpule 3 for forcing medicine out through a catheter needle assembly connected to the silicone body 4.

The flexible piston 5 is composed of segments hinged together and outwardly threaded guided by a rail 6 received in recesses in each of the segments of the rod 5. The not shown outward threads of the segments of the flexible piston rod 5 engage in a thread 8 of ratchet wheel 7 having teeth 9 along the periphery thereof. An electrical motor 10 electrically connected to a battery 11 and control means 12 is provided with a gear 13 meshing with a gear 14 attached to an outwardly threaded spindle or shaft 15 received in an inwardly threaded nut 16 attached a plate 17 provided with two slits 18 and 19, extending parallel to the axis of said spindle 15 and a third slit 20, extending at an angle to said axis. Two fixedly arranged pins 21 and 22 are received in the slits 18 and 19, respectively such that the pins serve as guides to the to and fro displacement of the plate 17 by means of the spindle 15 when the electrical motor 10 rotates first in one directional rotation and thereafter in the opposite directional rotation.

A protuberance 23 is arranged on the plate 17 to co-operate with two end stop contacts 24 and 25 electrically connected to the control means 12 for reversing the direction of rotation of the electrical motor when the protuberance 23 contacts one of the end stop contacts 24 or 25. A pawl 26 is attached to a pivotable elongated body 27 having a pin 28 for being received in the oblique slit 20 and a hole 29 for receiving the pin 21 such that the body 27 is pivotable around the pin 21. A ratchet 30 is fixedly attached to the housing 2 by means of a pin 31 and is located so as to engage the teeth 9 of the ratchet wheel 7. The pawl 26 is displaceable from a retracted position where it does not engage the teeth 9 of the ratchet wheel 7 and in an engaged position in which it engages the teeth of the ratchet wheel and rotates the ratchet wheel in a clockwise direction.

The displacement of the pawl 26 between the two positions indicated above takes place by the linear displacement of the plate 17. When the plate 17 is displaced in the direction from the end stop contact 24 to the end stop contact 25, the oblique slit 20 urges the pin 28 of the elongated body 27 in a direction away from the carpule 3 such that the elongated body 27 pivots around the pin 21 in a clockwise direction, whereby the pawl 26 is moved in towards its retracted position relative to the ratchet wheel 7. When the protuberance 23 on the plate 17 contacts the end stop contact 25, the directional rotation of the motor 10 is reversed and the plate 17 is displaced in the direction from the end stop contact 25 towards the end stop contact 24, whereby the oblique slit 20 forces the pin 28 towards the carpule 3, whereby the elongated body 27 is forced to rotate in a counterclockwise direction whereby the pawl 26 is brought into contact with one of the teeth 9 of the ratchet wheel and rotates the ratchet wheel in a clockwise direction, while the ratchet rides over one of the other teeth 9 for locking the ratchet wheel against rotation in the counterclockwise direction.

Thus, during one cycle of rotation in one direction and the opposite direction of the electrical motor 10, the ratchet wheel 7 will be advanced by one tooth corresponding to one displacement of the pawl 26 from the retracted position thereof to the engaged position thereof.

Referring now to FIGS. 6-9, in this embodiment a coil spring 40 is attached to a pin 41 fixedly attached to the housing 2 and a pin 42 fixedly attached to the plate 17.

When the plate 17 is moved in the direction from end contact 24 towards the end contact 25, the spring 40 is in tension, and when the plate 17 moves back in a direction from the end stop contact 25 towards the end stop contact 24 after reversion of the direction of rotation of the motor 10, the spring 40 will be relaxed and exert a force in the same direction as the motor 10 on the plate 17 and thus reinforcing the force available to rotate the ratchet wheel 7.

Referring now to FIGS. 10-15, the electrical motor 10 is electrically connected to a battery and control means and the axle of the motor is connected to a pair of twisted strings 35 or a band or similar device, which reduces its length when twisted and increases its length when untwisted, said length variation being provided by the rotation of the motor, i.e. the device is connected to the rotating axle of the motor at one end and connected to a pivotable body 78 at the opposite end. The pivotable body is provided with an extension 78a comprising a pawl 74 arranged to engage the teeth 9 on the ratchet wheel 7, as indicated in FIGS. 15a, 15b, 15c, whereby the pivoting of the pivotable body 78 provides a rotation of the ratchet wheel 7. A second pawl mechanism 72, 84 is provided to prevent rotation of the ratchet wheel 7 in the opposite direction, again as shown in FIGS. 15a-15c.

The displacement of the pawl 74 between the two positions indicated in FIGS. 15a and 15b is provided by the reduction of the length of the twisted strings 35 by rotation of the motor and the displacement in the opposite direction is provided by the spring 40 during extension of the twisted strings 35 provided by rotation of the motor in the opposite direction, whereafter further rotation in this direction again reduces the length of the twisted strings 35, whereby a complete cycle of rotation in one direction of the motor provides a movement of the pivotable body from the position shown in FIG. 15a to the position shown in FIG. 15b and back to the position shown in FIG. 15a, this movement being provided by the twisted strings 35 being untwisted and twisted in the opposite direction during rotation of the motor in one direction. Thus, the rotation of the motor in one direction of rotation provides a full stroke for the pivotable body and thus the pawl mechanism moving the ratchet wheel one step forward and the following rotation of the motor in an opposite direction of rotation provides a further full stroke of the pivotable body and the pawl mechanism.

Thus, during one cycle of rotation in one direction and the opposite direction of the electrical motor 10, the ratchet wheel 7 will be advanced by two teeth corresponding to two displacements of the pawl 74. The pivotable body 78 comprises a protuberance 78a which co-operates with two end stop contacts 85a and 85b electrically connected to the control means for controlling the reversal of the direction of rotation of the electrical motor when the protuberance 78a contacts the end stop contact 85a. Due to the fact that the twisted strings 35 can only provide a pulling force on the pivotable body 78, a spring 40 is connected to the pivotable body to provide the movement in the direction shown by the arrow in FIG. 10.

In the embodiment shown in the figures spring 40 is a coil spring, however, other types of springs, such as a rod spring could be provided for this purpose.

Figure 16:
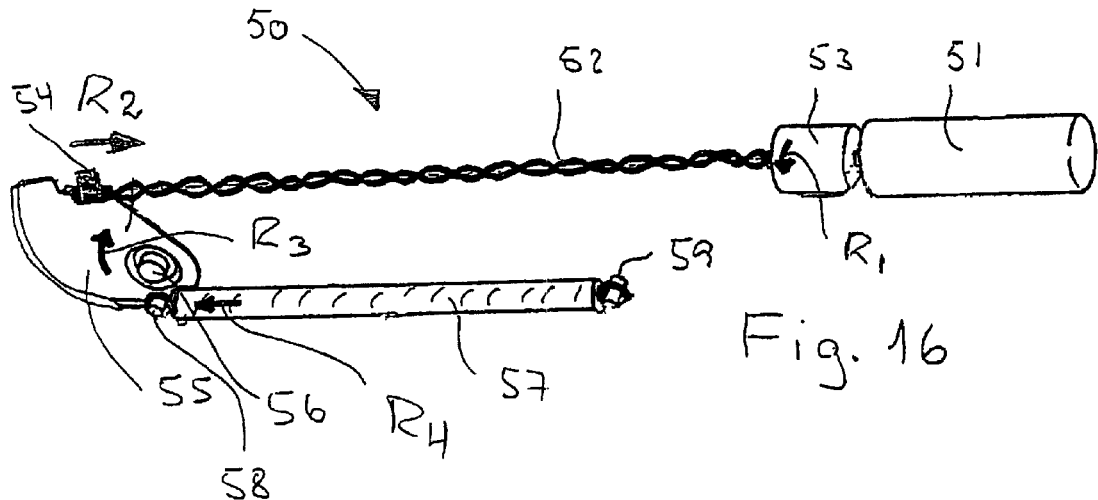
FIG. 16 is a schematic perspective view of a first embodiment of an actuator according to the invention, and FIGS. 17a-b very schematically show a second embodiment of an actuator according to the invention at two different phases of an actuation cycle.

Referring now to FIG. 16, an actuator according to the invention is referred to generally by the numeral 50 and is identical to the actuator shown in FIGS. 10-14. This actuator may be employed for any use requiring transformation of a rotation to a linear movement or a rotational force to a linear force.

A rotation motor 51 is attached to a pair of elongate, flexible elements such as strings or filaments 52 by means of a rotational body 53 that may or may not function as a fly wheel. The elements 52 are attached to a pin 54 on a pivotable plate. Rotation of the motor in the direction R1 will twist the strings 52 such that the length thereof is shortened until the pin 54 is displaced linearly in the direction R2 whereby the plate 55 is rotated around pivot 56 in the direction R3. A tension spring 57 is attached to plate 55 at pin 58 and to a not shown frame at pin 59.

Rotation of the plate 55 will expand the spring 57 in the direction R4 against the spring force thereof.

Rotation of the motor 51 in the direction opposite R1 will at first untwist the elements 52 whereby the length thereof becomes larger with the consequence that the spring 57 rotates the plate 55 in the direction opposite R3.

Further rotation of the motor 51 in the; direction opposite R1 will twist the elements 52 again an eventually exert a force on said pin 54 in direction R2 again, the direction of rotation being subsequently reversed again and the cycle starts anew.

In case, a smaller interval is desired between each turn of the plate 55 in the direction R3, the motor 51 may reverse direction of rotation as soon as the elements 52 have become untwisted to an extent that the spring 57 has pivoted the plate a certain distance in the direction opposite R3.

Figure 17A:
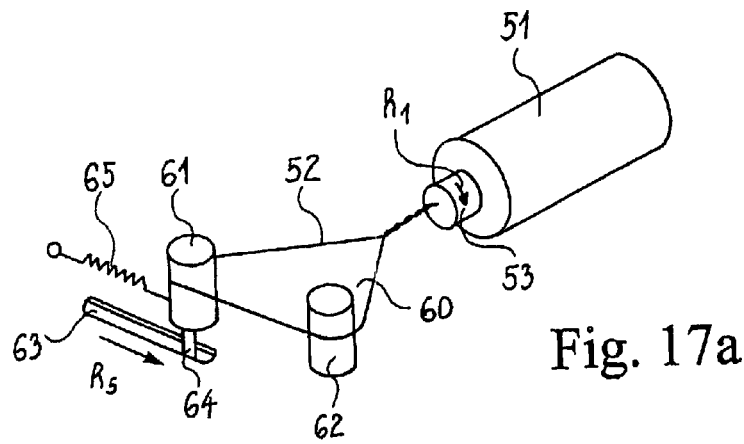
Figure 17B:
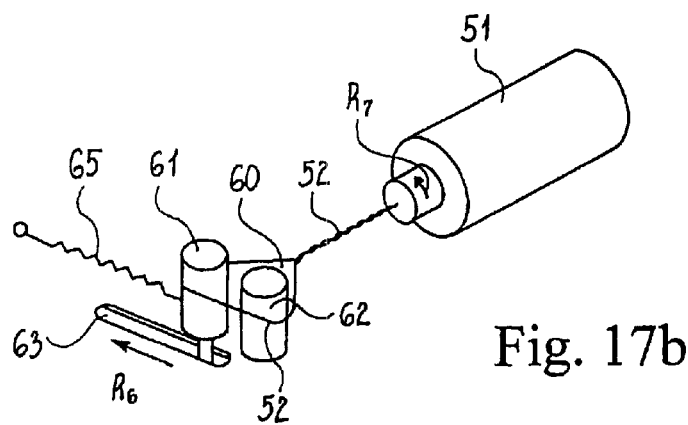

Reference is now made to FIGS. 17*a*-17*b*, where a motor 51 is attached to both opposed ends of an elongate, flexible element such as a string or filament 52 by means of a rotational body 53 that may or may not function as a fly wheel. The element 52 forms a loop 60 within which are located two bodies 61 and 62.

The body 61 is displaceable along a groove 63 in which a pin 64 of the body is slideably received. A spring 65 is attached to the displaceable body 61 such that displacement of said body 61 in the direction R5 takes place against the biasing force exerted by the spring 65.

The other body 62 is fixedly arranged such that when twisting of the element 52 by rotation of the motor 51 takes place the loop 60 is reduced in size as seen in FIG. 17*b* and the displaceable body 61 is forced towards the fixed body 62 along the groove 63 and against the spring force of the spring 65.

When the rotational direction of the motor is reversed so that it rotates in the direction R7, the element 52 will be untwisted, the loop 60 will enlarge and the spring 65 will displace the body in the direction R6.

Although the groove is shown extending substantially linearly, it may obviously be curved and extend at different angles to the axis of the motor.

The body 61 may be attached to a multitude of different driving or transmission mechanisms, for example the ratchet and pawl mechanisms shown in FIGS. 1-9.

A displaceable body should be taken to mean any body that can change position either by linear motion, curved motion, rotative motion, etc. and any combination thereof under the influence of a force applied to a point on or in said body.

Displacement should likewise be taken to mean any change in position resulting from linear motion, curved motion, rotative motion, etc. and any combination thereof.

The invention claimed is:

1. A wearable medicine dispenser device, comprising:
   a piston rod to force medicine from the device;
   a drive mechanism to advance the piston rod, the drive mechanism comprising a pawl and a driven member, the pawl positioned to engage one or more teeth of the driven member, wherein the pawl is adjustable between a first position and a second position to incrementally advance the driven member; and
   a rotational motor coupled to the pawl so that the pawl is at least partially adjusted toward one of the first position or the second position in response to one or more full rotations of the rotational motor.

2. The wearable medicine dispenser device of claim 1, further comprising an elongate string member coupled to the pawl and coupled to the rotational motor.

3. The wearable medicine dispenser device of claim 2, wherein one or more full rotations of the rotational motor causes the string member to act upon the pawl.

4. The wearable medicine dispenser device of claim 2, wherein the pawl comprises a pivotable body.

5. The wearable medicine dispenser device of claim 2, wherein the elongate string member comprises a flexible element selected from the group consisting of: a string, a filament, a strip, and a ribbon.

6. The wearable medicine dispenser device of claim 1, further comprising a bias member coupled to the pawl to urge the pawl toward the second position and incrementally advance the driven member.

7. The wearable medicine dispenser device of claim 6, wherein the rotational motor pivots the pawl toward the first position in response to one or more full rotations of the rotational motor.

8. The wearable medicine dispenser device of claim 1, further comprising a housing that defines a cavity to receive a medicine container.

9. The wearable medicine dispenser device of claim 8, wherein the piston rod is advanced toward the medicine container when the medicine container is received in the cavity.

10. The wearable medicine dispenser device of claim 1, further comprising a control circuit device to repeatedly reverse the direction of rotation of the rotational motor.

11. The wearable medicine dispenser device of claim 1, wherein the driven member is a ratchet wheel.

12. The wearable medicine dispenser device of claim 11, wherein the pawl is adjustable to the first position in which the pawl is retracted away from one or more teeth of the ratchet wheel.

13. The wearable medicine dispenser device of claim 1, further comprising a linearly displaceable plate coupled to the pawl and coupled to the rotational motor.

14. The wearable medicine dispenser device of claim 13, wherein one or more full rotations of the rotational motor causes the linearly displaceable plate to act upon the pawl.

15. A wearable medicine dispenser device, comprising:
    a piston rod to force medicine from the device;
    a drive mechanism to advance the piston rod;
    an elongate string member coupled to the drive mechanism; and
    a rotational motor coupled to the string member so that one or more full rotations of the rotational motor causes the string member to adjust the drive mechanism to advance the piston rod.

16. The wearable medicine dispenser device of claim 15, wherein the drive mechanism comprises a pawl and a driven member, the pawl positioned to engage one or more teeth of the driven member to incrementally advance the driven member.

17. The wearable medicine dispenser device of claim 16, wherein the pawl comprises a pivotable body that is connected with the elongate string member.

18. The wearable medicine dispenser device of claim 17, wherein the one or more full rotations of the rotational motor twists the string member and causes the string member to pull upon the pivotable body to thereby adjust the pawl relative to the driven member.

19. The wearable medicine dispenser device of claim 16, wherein the driven member is a ratchet wheel.

20. The wearable medicine dispenser device of claim 19, wherein the pawl is positioned to engage one or more teeth of the ratchet wheel so as to incrementally rotate the ratchet wheel in a driving direction.

21. The wearable medicine dispenser device of claim 20, further comprising a second pawl positioned to engage the one or more teeth of the ratchet wheel to inhibit rotation of the ratchet wheel opposite the driving direction.

22. The wearable medicine dispenser device of claim 15, further comprising a housing that defines a cavity to receive a medicine container.

23. The wearable medicine dispenser device of claim 22, wherein the piston rod is advanced toward the medicine container when the medicine container is received in the cavity.

24. The wearable medicine dispenser device of claim 15, wherein the elongate string member comprises a flexible element selected from the group consisting of: a string, a filament, a strip, and a ribbon.

25. The wearable medicine dispenser device of claim 15, wherein the string member comprises a loop such that the one or more full rotations of the rotational motor twists the loop.

26. The wearable medicine dispenser device of claim 15, further comprising a control circuit device to repeatedly reverse the direction of rotation of the rotational motor.

27. A wearable medicine dispenser device, comprising:
a housing that defines a cavity to receive a medicine container;
a piston rod movable in a forward direction toward the medicine container when the medicine container is received in the cavity;
a drive mechanism to advance the piston rod in the forward direction, the drive mechanism comprising a pawl and a ratchet wheel, the pawl positioned to engage one or more teeth of the ratchet wheel, wherein the pawl is pivotable between a first position and a second position to incrementally advance the ratchet wheel;
a bias member coupled to the pawl to urge the pawl toward the second position to incrementally advance the ratchet wheel;
an elongate string member coupled to the pawl; and
a rotational motor coupled to the string member so that one or more full rotations of the rotational motor causes the string member to twist and thereby urge the pawl toward the first position.

28. The wearable medicine dispenser device of claim 27, further comprising a second pawl positioned to engage the one or more teeth of the ratchet wheel to inhibit rotation of the ratchet wheel opposite the driving direction.

29. The wearable medicine dispenser device of claim 27, wherein the elongate string member comprises a flexible element selected from the group consisting of: a string, a filament, a strip, and a ribbon.

30. The wearable medicine dispenser device of claim 27, wherein the string member comprises a loop such that the one or more full rotations of the rotational motor twists the loop.

31. The wearable medicine dispenser device of claim 27, further comprising a control circuit device to repeatedly reverse the direction of rotation of the rotational motor.

32. A method of dispensing liquid medicine, comprising:
in a dispensing cycle, rotating a motor one or more full revolutions in a first rotational direction to twist or untwist a string member and thereby adjusting a ratchet mechanism coupled to a piston rod, wherein the adjustment of the ratchet mechanism incrementally advances the piston rod in a forward direction to force medicine from a wearable medicine dispenser device; and
in a next dispensing cycle, rotating the motor one or more full revolutions in an opposite, second rotational direction to twist or untwist the string member and thereby adjusting the ratchet mechanism coupled to the piston rod, wherein the adjustment of the ratchet mechanism incrementally advances the piston rod in the forward direction to force medicine from the wearable medicine dispenser device.

33. The method of claim 32, wherein the ratchet mechanism comprises a pawl and a driven member, the pawl being positioned to engage one or more teeth of the driven member to incrementally advance the driven member.

34. The method of claim 33, wherein the pawl comprises a pivotable body that is connected with the string member, said rotating of the motor twists the string member and causes the string member to pull upon the pivotable body to thereby adjust the pawl relative to the driven member.

35. The method of claim 32, wherein the wearable medicine dispenser device comprises a housing that defines a cavity to receive a medicine container, the piston rod being advanced in the forward direction toward the medicine container when the medicine container is received in the cavity.

* * * * *

UNITED STATES PATENT AND TRADEMARK OFFICE
CERTIFICATE OF CORRECTION

PATENT NO. : 7,713,238 B2
APPLICATION NO. : 10/591190
DATED : May 11, 2010
INVENTOR(S) : Morten Mernoe It is certified that error appears in the above-identified patent and that said Letters Patent is hereby corrected as shown below:

Column 1, lines 7-8, please delete "PA 2005 005423" and insert --PA 2005 00542-- therefor.

Signed and Sealed this

Third Day of August, 2010

David J. Kappos
*Director of the United States Patent and Trademark Office*